United States Patent [19]

Balassa

[11] 4,350,682
[45] Sep. 21, 1982

[54] CARTILAGE EXTRACTION PROCESSES AND PRODUCTS

[75] Inventor: Leslie L. Balassa, Blooming Grove, N.Y.

[73] Assignee: Lescarden Ltd., Goshen, N.Y.

[21] Appl. No.: 137,547

[22] Filed: Apr. 4, 1980

Related U.S. Application Data

[63] Continuation-in-part of Ser. No. 38,051, May 11, 1979, abandoned.

[51] Int. Cl.³ ..................... A61K 7/025; A61K 35/12; A23L 1/30
[52] U.S. Cl. ............................... 424/64; 424/DIG. 5; 424/14; 424/32; 424/95; 424/168; 424/177; 424/358; 424/359; 426/648; 426/655; 426/657
[58] Field of Search ................ 424/64, 95, 14, DIG. 5

[56] References Cited

U.S. PATENT DOCUMENTS

| | | | |
|---|---|---|---|
| Re. 28,093 | 7/1974 | Balassa | 424/95 |
| 2,320,098 | 5/1943 | Quisling | 424/64 X |
| 3,033,755 | 5/1962 | Jacobi | 424/64 X |
| 3,400,199 | 9/1968 | Balassa | 424/95 |
| 3,476,855 | 11/1969 | Balassa | 424/95 |
| 3,478,146 | 11/1969 | Balassa | 424/95 |
| 3,551,560 | 12/1970 | Thiele | 424/95 |
| 3,703,575 | 11/1972 | Thiele | 424/95 |
| 3,772,432 | 11/1973 | Balassa | 424/95 |
| 3,966,908 | 6/1976 | Balassa | 424/95 |

FOREIGN PATENT DOCUMENTS

| | | | |
|---|---|---|---|
| 3186M | 3/1965 | France | 424/95 |
| 476495 | 9/1969 | Switzerland | 424/64 |

OTHER PUBLICATIONS

Prudden et al., 1963, vol. 86, Archives of Surgery.
Houck et al., 1963, vol. 51, pp. 632–638.
Inoue, 1961, vol. 82, pp. 432–434.
Prudden et al., 1957, Surgery, Gyn, Obs., vol. 105, pp. 283–286.

*Primary Examiner*—Dale R. Ore
*Attorney, Agent, or Firm*—Darby & Darby

[57] ABSTRACT

A biologically active cartilage product is prepared by heating a mixture of crude animal or fish cartilage in water under pressure to form an aqueous cartilage extract, removing suspended matter from the extract and concentrating the extract under vacuum. The product may be dried to form a fine granular material.

27 Claims, No Drawings

CARTILAGE EXTRACTION PROCESSES AND PRODUCTS

This application is a continuation in part of my co-pending application Ser. No. 038,051 filed May 11, 1979, now abandoned.

This invention pertains to cartilage extraction processes and products. More specifically, the invention relates to a process for preparing a biologically active cartilage product using raw animal or fish cartilage together with adhering tissue as the starting material.

The preparation of powdered cartilage products for various therapeutic applications is discussed in the prior art. Thus, U.S. Pat. Nos. 3,400,199 and 3,772,432 teach the preparation of pharmaceutical materials from raw cartilage. In the preparation of these prior art products it was considered important to remove the adhering tissue (mainly proteinaceous and fatty tissues) from the raw cartilage material by pre-treatment with a suitable proteolytic enzyme solution. Thus, the raw cartilage material might be treated with a solution of pepsin and an acid (e.g., acetic or hydrochloric) at a temperature of about 50° C. for about five hours. After the adhering tissues had been removed the clean cartilage was vacuum dried, de-fatted with a suitable solvent (e.g., hexane), the solvent evaporated and the cartilage mechanically comminuted to a fine powder of between about 5 to 40 microns average particle size. The cartilage powder so obtained could be utilized in powder form or, extracted at a temperature between about 3° to 4° C. with distilled water or an aqueous salt solution which facilitated solubilization or peptizing of the cartilage material at low temperature. The solubilized cartilage obtained in this manner is not a true solution but rather consists of a colloidal dispersion containing between about 1 and 10% cartilage solids.

Because of the complexity and number of steps required for preparation, cartilage products prepared according to the prior art processes are relatively expensive materials. The resulting materials also suffer from several significant drawbacks. Solutions containing solubilized cartilage materials are generally opaque. Although it has been recognized that the opacity is attributable to a small quantity of suspended particles (of larger than colloidal size) they are difficult to remove from cold solutions (either by centrifuging or filtration) without simultaneously incurring substantial losses of active material. Since it was found that the presence of oxygen during the extraction process tended to degrade the resulting extract, and lower its biological activity, it was believed necessary to maintain a low temperature oxygen-free environment during cartilage processing steps in order to avoid degradation and loss of biological activity in the finished product. An important element of prior art processing operations involved grinding the cartilage material to a predetermined average particle size, an expensive and time-consuming operation.

It has now been surprisingly discovered that cartilage preparations having high biological activity can be obtained by extracting crude, mechanically trimmed cartilage (i.e., cartilage which still retains a portion of the adhering tissues—primarily proteinaceous and fatty tissues) together with water, under heat and pressure, for a predetermined time period. In contrast with prior processes, it has been unexpectedly discovered that cartilage materials need not be processed at low temperatures or in a completely inert, oxygen free atmosphere, but can be processed at high temperatures (from about 50° C. up to about 150° C.) and pressures (between about 10 and about 60 PSI) to yield extracts possessing high biological activity. As a further advantage the process of the present invention dispenses with the requirement of a pre-extraction grinding operation thereby substantially reducing processing costs. However, pre-extraction grinding can be optionally employed under certain processing conditions to yield a desirable product.

According to the present invention, cartilage products having high biological activity are prepared by heating a mixture of crude cartilage and water under pressure and substantially non-oxidizing conditions for a predetermined period of time to form an aqueous cartilage extract, removing suspended solid matter from the extract and concentrating the extract under vacuum. As employed herein the term "substantially non-oxidizing conditions" refers to controlled environments in which small quantities, on the order of a few percent or less (by volume) of air or oxygen may be present. The concentrated extract, which may be in gel or liquid form, can be dehydrated using any of several techniques, to yield a friable granular material which forms clear or slightly hazy solutions with water. The solid and liquid cartilage products of the present invention are useful as ingredients in various pharmaceutical and cosmetic compositions.

It is accordingly an object of the present invention to provide a process for preparing cartilage products from raw cartilage.

Another aspect of the present invention relates to the preparation of a new cartilage products that are useful in various pharmaceutical and cosmetic applications.

A still further aspect of the present invention involves a method for using cartilage products prepared according to the present invention in pharmaceutical formulations for the treatment of pruritus ani and hemmorhoidal conditions.

These and other objects of the present invention will become apparent upon consideration of the following detailed description of the invention.

The present invention involves a process for the preparation of cartilage products from raw animal or fish cartilage. As used herein, the term "raw cartilage" refers to cartilage from which the adhering tissues (primarily proteinaceous and fat) has not been separated or removed. Bovine cartilage (especially bovine tracheal cartilage) is the preferred raw material for use in the invention, however cartilage taken from other vertebrate animals including procine and canine cartilage as well as cartilage from the partly calcified skeleton, including fetal skeleton, of very young or newly born animals will also provide suitable results. Cartilage from young animals or young or newly regenerated cartilage from older animals has also been found satisfactory for use in the present invention. Cartilage from mature animals in either the form which would in maturity retain the cartilaginous form or which would in maturity ossify to bone may also be employed. Skeletal cartilage from fish, particularly the shark, has also been found to provide an especially satisfactory raw material.

Cartilage from the skeletons of shark or other cartilaginous fish may be used to prepare aqueous cartilage extracts in the same manner as bovine cartilage. However, in the case of the shark, the spinal column is the most convenient tissue to harvest. Despite the fact that in most sharks the vertebrae are calcified to a considerable degree, they contain sufficient cartilage material to yield a useful extract. While bovine trachea is the preferred source of raw cartilage, as it is the most readily accessible cartilaginous tissue in mammals, hyaline or costal cartilage from other parts of the animal's body may be utilized to produce satisfactory extracts.

The raw cartilage may be prepared by any satisfactory means but generally is obtained by removing substantially all of the skin, integument and organs of the animal or fish and separating the cartilage. The separated cartilage, to which some proteinaceous tissue and fat will generally still be adhered may be subdivided into chunks or used in whole form as removed from the animal. It is not necessary to remove all vestiges of adhering tissue, as in prior art cartilage processing techniques. The size of the raw cartilage to be employed in the invention is not critical and is primarily dependent upon the dimensions of the reaction vessel in which the cartilage is to be processed.

The raw cartilage is mixed with water in the ratio from 1:100 to 100:1 and preferably 1:2 to 2:1 by weight (cartilage:water). Preferably the water is deionized or distilled. The mixture of raw cartilage and water is transferred to a suitable pressure vessel (e.g., a steam pressure vessel), fitted with a pressure relief valve and the vessel heated to a temperature of between 50° C. and 150° C. and preferably between about 105° C. and 125° C. or until a pressure of 10 to about 60 p.s.i.g., and preferably between about 10 to about 30 p.s.i.g. (pounds per square inch—gauge reading) of steam has been built up within the vessel. The preferred extraction condition is 20 p.s.i.g. pressure for two hours (at a temperature of about 110 degrees C.). However, reaction periods of between 5 minutes and 5 hours may be employed to yield satisfactory results. Under optimum conditions the extraction is continued to the point at which the cartilage substance has just become completely dissolved, but the aqueous extract is still a light tan color and has not acquired a dark brown color. The connective, fibrous and fatty tissues adhering to the raw cartilage are extracted, but not solubilized, during the heat and pressure treatment.

Substantially all of the fat contained in the cartilage, and adhering tissues, is released during the extraction under heat and pressure, and floats to the surface of the extract. The insoluble fibrous tissues containing a minor portion of fat will generally sink to the bottom of the reaction vessel.

At the conclusion of the heat and pressure treatment, the vessel is opened and the aqueous cartilage extract removed. The solid matter consisting primarily of fibrous tissues and fat is separated from the extract by centrifuging. In some instances, the solids may be removed by decanting the extraction liquid. A small portion of the fatty content of the raw cartilage remains emulsified in the extract and may be removed either by prolonged centrifuging at very high speeds (centrifugal pressures of 1,000 G's or more). Alternatively, the emulsified fat is removed by filtering through a filter press coated with a diatomaceous earth filter aid. The filtrate (or the liquid recovered from the centrifuge) has a clear amber color. Analysis of the recovered extract shows it to be rich in proteinaceous material and low in calories. The extract is suitable for use as a dietary food supplement or a health food.

The filtered or centrifuged extract is concentrated by removing a portion of the moisture content under vacuum in a mechanically agitated thin film evaporator. Thin film evaporator devices are well known in the art and utilizes rotating slotted wiper blades to generate a thin film of liquid on the heated wall of a sealed vessel. The slots in the rotating wiper blades provide a pumping action which creates and moves the thin liquid film along a heated wall with constant agitation. As the concentrating residue travels downward, it is in continuous contact with the evaporating surface from which vapor is continuously separated. The vapor travels through a rotating entrainment separator to the surface of an internal condenser where it is condensed and flows by gravity to an outlet valve. The action of the wiper blades in moving the residue down and off the heated wall eliminates thermal degradation by controlling the residence time at the distillation temperature. The concentration is conducted under a vacuum of between about 10 and 100 torr (millimeters of mercury) and a jacket temperature of between about 90 and 180 degrees C.

A wiped film (or thin film) evaporator apparatus suitable for use in the present invention is available from the Pfaudler Company, 1000 West Avenue, Rochester, N.Y. as a 12 inch diameter model WFE with four square foot heating surface, Teflon wiper blades, Denison fluid motor MF05-014 and an 11 square foot internal condenser. The aqueous cartilage filtrate (or centrifugate) is concentrated under vacuum, preferably of 40 tor (absolute) to yield a liquid of between about 45 to 65% solids content. The viscosity of the liquid will vary depending upon the temperature and solids content. Thus the liquid may be readily flowable and of low viscosity at higher temperatures and low solids content, and conversely may be in gel form at low temperatures and with a higher solids content.

The liquid concentrate (which is partially dehydrated product) may be used as such in various cosmetic, pharmaceutic and food products or it can be completely dehydrated to a dry granular substance. Suitable dehydrating techniques include freeze drying, vacuum spray drying, dehydration with a liquid (e.g., ethanol, isopropanol); azeotropic distillation with a hydrocarbon azeotrope (e.g., hexane). In making a product to be used in the manufacture of an injectable cartilage extract it is preferable to combine the liquid concentrate with an excess of isopropanol to precipitate the active ingredients of the cartilage extract as a solid.

The completely dehydrated extract is a friable granular or lumpy material which is generally of a light tan color. The dry material can be readily ground to yield a fine powder and dissolves readily to form clear or slightly hazy solutions with water.

The cartilage extracts of the present invention in either the dry or liquid form have been found to be especially useful in the treatment of hemmorhoidal conditions and pruritus ani. The liquid extracts are also useful as geriatric and dietary food supplements because of their high protein and low fat content. The extracts may be prepared in liquid or dry form for use as an ingredient (e.g., skin conditioner) in cosmetic formulations.

The biologically active agent of the invention may be administered in the form of a liquid, as a suspension or solution, or alternatively in solid form as a tablet pellet or capsule. The tablet may be prepared using conventional tabletting procedures in which the active ingredient is combined with well known pharmaceutical excipients such as starch, sugar, bentonite clays and other commonly used carriers. Satisfactory pharmaceutically acceptable liquids include water, sugar solutions, and aqueous glycols which may be compounded with coloring agents and synthetic or natural flavors. In another embodiment, the dry active ingredient may be incorporated onto silica gel or other gel forming materials which are capable of coating the stomach walls. The active ingredient may also be administered as a suppository, or a topically applied cream, or ointment. A preferred embodiment of the invention useful for treating hemorrhoidal conditions involves rectal administration of the active ingredient in the form of a shaped suppository.

For the preparation of cartilage extracts that may be administered by parenteral injection, it is desirable to remove as much of the adhering tissue and fat as possible from the starting cartilage material prior to the high pressure extraction step. This is accomplished by mixing the raw cartilage in a digestive solution containing proteolytic enzymes (preferably acid-pepsin). Trypsin and pepsin exemplify the wide variety of proteolytic enzymes that are useful in this aspect of the invention. Following the enzyme pretreatment, the digested cartilage can then be extracted under high temperature and elevated pressure. Although the pretreated materials or cartilage extracts prepared can be used for food additives, cosmetic applications and in topical and oral preparations, it is not desirable to do so, as the enzyme pretreatment results in the loss of some biologically active material from the new cartilage. This loss occurs when the cartilage is leached in the enzyme bath and during the subsequent washing operations. Also, the pretreatment adds significantly to the cost of the finished product.

In preparing a cosmetic composition in accordance with the present invention, any suitable cream, emulsion or oil cosmetic base, which will keep the cartilage material in solution or suspension may be used. The base may be in emulsified form including waxes, oils, emollients, preservatives and humectants, or may be in the form of a vegetable oil, or mixture of vegetable and mineral oils or mixture of oil and water based compositions.

The following examples illustrate certain preferred embodiments of the invention. However, it should be understood that these examples are non-limiting illustrations and that other methods and embodiments are envisioned by the present invention. Parts and ratios are by weight except as otherwise stated.

EXAMPLE I

Extraction of bovine trachea 5 kilograms of deionized water was admixed with 5 kilograms of well trimmed beef trachea subdivided into pieces of about 3 inches in the largest dimension. The water/trachea mixture was loaded into a 20 liter aluminum pressure vessel equipped with a pressure gauge and a pressure relief valve. The vessel was sealed, the lid clamped shut, but the relief valve left open. The vessel was heated to about 100° C. to bring the water to a boil and the relief valve left open until the steam generated by the boiling water had displaced substantially all of the air from within the vessel. The relief valve was then closed and the steam pressure allowed to rise to about 20 p.s.i.g. (temperature 110° C.) with the actual pressure fluctuating between about 17 and 25 p.s.i.g. (105°–116° C.). The pressure and temperature was held constant for two hours. The vessel was then allowed to cool to atmospheric pressure, the pressure valve opened and the lid of the vessel removed. The partially processed trachea were thoroughly mixed, the lid replaced, and the liquid again brought to a boil. Air was purged from the vessel by means of steam generation as outlined previously, the pressure brought to 20 p.s.i.g. and held at that level for another two hour period. The vessel was again cooled to ambient temperature, the pressure valve opened, the lid removed and the liquid contents of the vessel strained through a 100 mesh stainless steel strainer. The strained liquid was centrifuged in order to remove the major part of the suspended matter. The yield was as follows:

| | |
|---|---|
| Liquid Extract | 7500 grams |
| Fat | 850 grams |
| Fibrous protein matter with some fat | 1600 grams |

The fibrous matter residue contains 50% liquid which was expressed to increase the yield of the liquid extract. The liquid extract contains 8% non-volatile dry extract which includes about 1% suspended fat (emulsified) and protein. The remaining 7% represents 525 grams dry weight, or 10.5% based on the weight of the trachea. The liquid extract was a cloudy light tan colored fluid at ambient temperature but consolidated to form a firm gel upon refrigeration to 10° C. or lower.

The liquid was found to be stable upon storage under sterile conditions or when protected with a suitable preservative (e.g., benzyl alcohol or a combination of sorbic acid and sodium benzoate). The extract had a pleasant taste, characteristic of meat extract and which could be enhanced by seasoning with salt, pepper, or other condiments customarily employed for seasoning soups or meat products. The extract was suitable for use as a dietary food supplement or could be administered as a pharmaceutical preparation.

EXAMPLE II

The liquid extract of Example I was concentrated to 45% non-volatile solids content under vacuum (40 mm of Hg) and mechanical agitation at a jacket temperature of 120° C. in a thin film evaporator (Pfaudler model WFE). The liquid material formed a very firm gel when cooled to 15° C. or lower. The material had a pleasant taste and was ingested as a dietary food supplement. The gel was also useful as a moisturizing component in conventional cosmetic cream and ointment formulations.

EXAMPLE III

The concentrated extract (45% solids) of Example II was evaporated to dryness in a laboratory oven (110° C.) and under 40 millimeters of vacuum. The dried material, which was hard and brittle, was pulverized. The pulverized material was used to fill one thousand 50 milligram hard shell gelatin capsules. The capsules were suitable for oral administration. The powder was also used to make shaped rectal suppositories for administration to humans to alleviate pruritus ani and hemmorhoidal inflammation (see Example IX).

EXAMPLE IV 2200 pounds of bovine trachea was quartered and ground in a Weiler (meat) grinder using a one-half inch orifice plate. After grinding, the material was transferred to a 100 gallon glass lined reactor equipped with a mechanized agitator. The liquid-trachea mixture was processed in six batches. The weight of trachea for each batch varied between 300 and 425 pounds. Deionized water was added to the reactor on a one-to-one weight ratio (1 pound of ground trachea to 1 part water). Internal pressure of the reactor was brought to between 15 and 24 p.s.i.g. (temperature 110° C.) after air purging and held for two hours with the agitator in operation (120 r.p.m.). The extracted mixture was removed from the pressure chamber and pumped-through a centrifuge type decanter (Flottweg Decanter Z-1L). The solids discharged from the decanter were collected, weighed and sampled. The extraction liquid that remained after the decanting operation was subjected to a three way separation in a Titan disc-type centrifuge—the separations yielded:

A. Light Liquid—grease
B. Heavy solids—sludge
C. Water phase—product

The product from centrifuge batch 1 and 2 was further processed through a filter press. The pH of the product obtained from centrifuge batches 3 through 6 was adjusted with glacial acetic acid to between about pH 5 and pH 5.5. The Titan disc centrifuge had a bowl speed of 6200 r.p.m. and an effective G force of more than 1,000 G's.

The product from batches 1 and 2, after filtration, was combined, the combined material decanted and centrifuged again in the disc centrifuge. Approximately ½% of benzyl alcohol was added to the combined product as a preservative. The products of batches 3 and 4 were combined as were the products of batches 5 and 6. The following analyses were performed:

| Raw Material (Material In) - in lbs. | | | | | | |
|---|---|---|---|---|---|---|
| Batch # | 1 | 2 | 3 | 4 | 5 | 6 |
| Trachea | 317 | 350 | 350 | 347 | 425 | 425 |
| Water | 317 | 382 | 350 | 347 | 425 | 457 |
| Total | 634 | 732 | 700 | 694 | 850 | 882 |

| Material Out - in lbs. | | | | | |
|---|---|---|---|---|---|
| Batch # | 1 & 2 | 3 | 4 | 5 | 6* |
| Decanter Solids | 81.5 | 40 | 41 | 53 | 84 |
| Cent. Eff. - Product | 1034 | 523 | 543 | 613 | 686 |
| Grease | 76 | 51 | 38 | 56 | 89 |
| Cent. Sludge | 19 | None | 21 | None | 20 |
| Total | 1210.5 | 614 | 649 | 722 | 879 |

*Between Batch 5 and 6 the product from batch 1 and 2, which had been filtered and contained filter earth, was reprocessed thru the decanter and centrifuge. Therefore, the decanter solids for Batch 6 contained some filter earth.

| | Material Balance | | | | | |
|---|---|---|---|---|---|---|
| | 1 & 2 | | 3 thru 6 | | 1 thru 6 | |
| Batch | Lbs. | % | Lbs. | % | Lbs. | % |
| Material in (total) | 1366 | — | 3126 | — | 4492 | — |
| Material out (total) | 1210.5 | 88.6 | 2864 | 91.6 | 4074.5 | 90.7 |
| Assume lost as steam | 155.5 | 11.4 | 262 | 8.4 | 417.5 | 9.3 |
| Decanter solids | 81.5 | 6.0 | 218 | 7.0 | 299.5 | 6.7 |
| Cent. Eff. - Product | 1034 | 75.7 | 2365 | 75.6 | 3399 | 75.7 |
| Grease | 76 | 5.6 | 234 | 7.5 | 310 | 6.9 |
| Cent. sludge | 19 | 1.4 | 41 | 1.3 | 60 | 1.3 |

ANALYSIS

The following analyses were performed:

Moisture: Volatile Material—The samples were dried in a forced air oven set at 105° C.

Fat Analysis—The dried samples were fat extracted with petroleum ether in a soxhlet extraction tube for a minimum of 2 hrs.

Protein Analysis—Protein analysis on the dried, fat-free samples. The boric acid modification of the Kjeldahl method for the determination of nitrogen was used. The following factors were used:

$$\% N_2 = \% NH_3/1.2158$$

| | Decanter Solids | | | | | | Centrifuge Extract | | | | | |
|---|---|---|---|---|---|---|---|---|---|---|---|---|
| | 1-2 | | 3-4 | | 5-6 | | 1-2 | | 3-4 | | 5-6 | |
| Batch | Dry | As Rec. | Dry | As Rec. | Dry | As Rec. | Dry | As Rec. | Dry | As Rec. | Dry | As Rec. |
| Moist. & Vol. | 0.0 | 73.8 | 0.0 | 72.3 | 0.0 | 72.3 | 0.0 | 83.7 | 0.0 | 83.3 | 0.0 | 84.6 |
| % Solids | 100.0 | 26.2 | 100.0 | 27.7 | 100.0 | 27.7 | 100.0 | 16.3 | 100.0 | 16.7 | 100.0 | 15.4 |
| % Fat | 7.6 | 2.0 | 8.9 | 2.5 | 6.7 | 1.9 | 5.7 | 0.9 | 6.6 | 1.1 | 3.6 | 0.6 |
| % Protein | — | — | 76.1 | 19.2 | 76.6 | 19.8 | — | — | 54.5 | 8.5 | 55.5 | 8.2 |

Approximately 100 gallons of liquid from centrifuge batches 1 and 2 were fed into the feed tank of a standard P faudler WFE 4 square foot wiped film evaporator set up with a louvered rotor having spring mounted wiper blades in which the outer jacket temperature was 173° C. The feed, a milky white, water-like liquid was heated by the outer jacket to 40.5° C. and the internal operating pressure of the evaporator reactor adjusted to 40 millimeters of mercury (absolute). The liquid was fed through the heated evaporator (173° C.) at a feed rate of 225 pounds per hour to yield a 70% distillate split (i.e. 70% of the water in the starting material was removed).

EXAMPLE V

| Blue shark spinal column | 5305 grams |
|---|---|
| Water, deionized | 5400 grams |
| Total charge | 10,705 grams |
| Yield | |
| Liquid Extract | 7300 grams |
| Insoluble calcified and proteinaceous residue | 3000 grams |

Process: Water was charged into a pressure vessel (as in Example I), heated to about 90° C. and sections of a blue shark spinal column (frozen) then added. The same heat and pressure extraction procedure was used in Example I, but the total heat and pressure treatment time was only two hours as the shark cartilage solubilized more quickly than the bovine cartilage. The liquid extract was centrifuged and then conducted through a filter press coated with a diatomaceous earth filter aid to remove suspended solid materials. The filtered extract had a light tan color and was almost transparent being essentially fat free. The extract is stable under sterile conditions or under ambient temperature conditions if suitable preservatives (e.g. benzyl alcohol ½-1%) are incorporated.

EXAMPLE VI

The process of Example V was repeated using sand shark spinal columns as the starting material. The yield and quality of the extract was substantially identical to that obtained in Example V.

EXAMPLE VII

Raw calf trachea was ground in a meat grinder to a $5^3$ mm average particle size and loaded into an extraction vessel. The extraction vessel used was a 4 liter jacketed stainless steel pressure vessel having a removable top and equipped with a steam inlet, a steam outlet valve, a pressure gauge, thermometer, a turbine mixer operating at 120 r.p.m., and a material inlet capable of introducing dry material against the prevailing pressure in the vessel. The vessel containing 500 ml of de-ionized water was preheated to the required temperature. The specified pressure was obtained by introducing into the vessel through the steam inlet valve. The air was substantially purged from the vessel with steam. The mixer was activated and the 500 grams of ground cartilage forced into the vessel with nitrogen. Satisfactory extracts were obtained at the pressures (in absolute psi), temperatures (in degrees Celsius), and extraction times (duration of treatment) given in the table below:

| PSI | °C. | Extraction Time |
| --- | --- | --- |
| 14.7 | 100 | 2 hours |
| 20 | 109 | 1.5 hours |
| 25 | 116 | 1 hour |
| 30 | 121 | 30 minutes |
| 35 | 126 | 20 minutes |
| 40 | 131 | 15 minutes |
| 50 | 138 | 10 minutes |
| 60 | 145 | 5 minutes |

EXAMPLE VIII

The following tests were performed utilizing the aforementioned vessel (Ex. VII) but replacing the turbine mixer with a homogenizing type enclosed turbine mixer, e.g. Barinco, Model CJ4A (Arde-Barencolo, Mahwak, N.J.), operated alternately in the upward mode and in the downward mode at a transformer setting of 80 which results in a speed of about 5000 r.p.m. In these tests, the pressure in the vessel was not allowed to rise above atmospheric pressure (14.7 p.s.i.) during extraction. The extraction condition (temperature and time) were varied for each extraction. The vessel was blanketed with an inert gas or non-oxidizing gas (nitrogen). The calf trachea was pre-ground to a $2^3$ mm average particle size to allow the mixer to operate at the closest rotor/stator setting thereby providing the highest possible whearing conditions. The following temperature/time schedules yielded satisfactory (biologically active) extracts under the above processing conditions.

| °C. | Time in Minutes |
| --- | --- |
| 50 | 60 |
| 75 | 30 |
| 90 | 20 |
| 100 | 10 |

By using a suitable homogenizing mixer, e.g. Barinco, Tekmar, Eli Dicon, Eppenbach etc., and ground cartilage, it is possible to extract the cartilage in a continuous manner at elevated temperatures and at atmospheric or only slightly elevated pressures. The resulting extracts are a pale amber color and show only minimal heat degradation.

EXAMPLE IX

Twenty male and 20 female patients ranging in age between 60 and 85 years received a dietic food supplement consisting of cartilage extract obtained from Example I herein. All of the patients suffered from joint pains and limited joint movement attributable to confirmed rheumatoid arthritic conditions. Each patient received a daily dose of the liquid cartilage extract of Example I at the equivalent rate of 8 grams per day or dry extract for a period of three months. The daily dosage was subdivided into three approximately equal size portions.

Thereafter the patients each received the liquid extract at the equivalent of 6 grams per day of the dry extract (subdivided into two doses of 3 grams) for three months. Thereafter each patient received the equivalent of 4 grams per day of the dry extract for a subsequent three month period. The cartilage material was self-administered via the oral route.

The physical condition of each patient was checked prior to commencement of the trial, daily for the first week, and once a week thereafter. Blood and urinalysis tests were conducted on each patient prior to the test to determine a baseline, and thereafter on a weekly basis. All patients reported that movement in the affected joints became less painful and the range of motion had increased between 7 and 30 days after commencement of the cartilage regime. Patients who discontinued the cartilage food supplement experienced a gradual return of their previous arthritic pain level wherein three to eight months. The periodic physical examinations and laboratory tests confirmed that the cartilage diet had no adverse effects on any patients' vital functions.

EXAMPLE X

Rectal suppositories were prepared using a hydrogenated vegetable oil base having a melting point of about 37° C. Two groups of one thousand two inch suppositories were prepared containing respectively 2%, and 5% vacuum dried cartilage extract powders obtained in Example III. The suppositories were administered to 40 patients in a double-blind study. 20 patients with confirmed hemmorhoidal lesions received active suppositories in two groups. The first group received suppositories containing 2% by weight (40 mg) of dried cartilage extract and the second group received suppositories containing 5% (100 mg) active ingredient. The control group of 20 persons received only a placebo consisting of a hydrogenated vegetable oil base of the same shape, color, size and weight as the active suppositories. Each patient received three suppositories a day at approximately six hour intervals for a period of three weeks. The test results revealed that the cartilage extract containing (active) suppositories were highly effective in reducing the inflammation and pain of the hemmorhoidal lesion. Patients receiving the active suppositories experienced fewer bleeding episodes and experienced rapid healing of small anal fissures. Those patients receiving placebo suppositories reported negligible effects attributable to the lubricating effect of the vegetable oil base.

EXAMPLE XI

Skin cream with cartilage extract as the active ingredient.

| Composition: | % by weight |
|---|---|
| Lanolin-acetylated | 2.50 |
| Petrolatum | 4.00 |
| Beeswax, bleached | 2.50 |
| Cetyl alcohol | 1.50 |
| Isopropyl myristate | 11.00 |
| Stearic acid | 1.50 |
| Mineral oil | 9.20 |
| Glycerol | 3.00 |
| Borax | 0.80 |
| Colloidal clay | 2.00 |
| Triethanol-amine | 1.40 |
| Sorbic acid | 0.20 |
| Benzyl alcohol | 0.90 |
| Cartilage extract, dry. Example III | 2.00 |
| Water, distilled | 57.50 |
| Total | 100.00 |

Procedure: The water was heated to about 80° C. The cartilage extract, borax, glycerol, triethanol-amine and sorbic acid were dissolved in the hot water. Using a high speed homogenizing mixer, the colloidal clay and stearic acid were dispersed. The balance of the ingredients were then dispersed in the aqueous medium. The resulting cream was then allowed to cool to ambient temperature. Cosmetic creams exhibiting high moisture retention qualities in the skin were obtained when 2 to 4% by weight of cartilage extract solids were incorporated into the cream. Similar results were obtained when the cartilage extract employed was a liquid extract of 8% solids content (as in Example I) the 45% concentrate of Example II or the extracts, liquid or dried, obtained in Example III and IV. The shark cartilage of Example VII was used after it was deodorized by steaming.

EXAMPLE XII

Shaped lipsticks were prepared utilizing conventional techniques and standard cosmetic bases comprising hydrogenated vegetable oils, lanolin waxes, lanolin alcohols, beeswax and petrolatum. Into such bases cartilage extracts were incorporated in quantities of 2 to 10% by weight based on the dry extract (prepared as in Exh. III). The lipsticks were pleasant on the lips and had an effective emollient action. In use they effectively prevented development of chapped lips and hastened the healing of cracked lips. The therapeutic lipsticks also accelerated the healing of herpes simplex lesions ("cold sores") on the lips.

EXAMPLE XIII

The following cosmetic facial creams were prepared utilizing the cartilage extract of Example I.

| CREAM A | | % | Gr. |
|---|---|---|---|
| (I) | Modulan (Acetylated Lanolin - Amerchol Corp.) | 3.0 | 600 |
| | White petrolatum | 5.0 | 1000 |
| | Beeswax | 3.0 | 600 |
| | Isopropyl Myristate | 8.5 | 1700 |
| | Cetyl alcohol | 2.0 | 400 |
| | White mineral oil | 6.5 | 1300 |
| | Stearic Acid | 2.0 | 400 |
| | Oil base | 30.0 | 6000 |
| (II) | Distilled water | 35.0 | 7000 |
| | Borax | 0.7 | 140 |
| | Veegum (colloidal clay - R.T. Vanderbilt Co.) | 1.5 | 300 |
| | Titanium dioxide | .2 | 40 |
| | Triethanolamine | .2 | 40 |
| | Cartilage extract (Ex. I) | 1.2 | 240 |
| | Benzyl Alcohol | 25.0 | 5000 |
| | Glycerol | .9 | 180 |
| | | 5.3 | 1060 |
| | Water base | 70.0 | 14000 |

I and II were prepared separately. Both were heated to 70° C. and I slowly added to II under constant mixing of II with a Barinco mixer (Arde-Barinco Corp., Mahwah, N.J.).

The resulting material, a cosmetic cream of uniform consistency, was packed in 50 ml glass bottles and the bottles sealed with threaded covers.

| CREAM B | | |
|---|---|---|
| (I) | Modulan | 300 |
| | White Petrolatum | 500 |
| | Beeswax | 300 |
| | Isopropyl myristate | 870 |
| | White mineral oil | 700 |
| | Stearic Acid | 200 |
| | Oil base | 2870 |
| (II) | Deionized Water | 3500 |
| | Titanium Dioxide | 80 |
| | Sorbic Acid | 20 |
| | Carbopol 934 | 46 |
| | Urea | 300 |
| | Triethanolamine | 125 |
| | Benzyl alcohol | 80 |
| | Cartilage extract (Ex. I) | 2500 |
| | Water Base | 6651 |

II was placed in a vessel equipped with a Barinco Mixer, deionized water added and the mixture heated to 70°–80° C. followed by addition of $TiO_2$, sorbic acid and Carbopol. The ingredients were mixed to obtain a uniform dispersion. Urea was then added and mixing continued while the Triethanolamine, cartilage extract and benzyl alcohol were added. Then under constant mixing molten (I) was added and the combined ingredients mixed until a smooth homogeneous emulsion was obtained.

Cream B was packaged in 50 ml bottles, and the bottles sealed with threaded covers.

Both creams (A and B) were topically applied on a daily basis to the facial area by a group of 20 women for a period of about 3 months. There was a general increase in turgor of the skin and all 40 participants (20A and 20B) reported satisfactory skin toning and moisturization effects with the respective cosmetic formulations.

EXAMPLE XIV

Extraction of bovine trachea—Ratio of water to trachea 1/100

50 grams of dionized water was admixed with 5 kilograms of well trimmed beef trachea that had been subdivided into pieces of about 1 inch in the largest dimension. The water/trachea mixture was loaded into a jacketed stainless steel pressure vessel having a 20 liter capacity. The vessel was equipped with a variable speed stainless steel turbine mixer, a steam inlet valve, theremometer, pressure gauge and pressure relief valve. The vessel was sealed, the lid clamped shut and the relief valve left open. Steam was introduced into the jacket and the mixer activated at a speed of about 20 RPM. When the temperature in the vessel reached 100° C. the steam valve leading into the vessel was opened and a slow stream of moist steam introduced and kept on for about three minutes until substantially all of the air in the vessel had been purged. Both the steam valve and the pressure relief valve were then closed and the stem pressure in the jacket increased to 23 p.s.i.g. This brought the internal pressure in the vessel to 20 p.s.i.g. This pressure was maintained for 4 hours and the speed of the mixer increased to 60 RPM after the first 30 minutes. The vessel was cooled to ambient temperature by circulating cold water through the jacket. The pressure valve was opened, the lid removed and the contents of the vessel strained through a 100 mesh stainless steel strainer while they were still hot (90° C.). The fibrous matter retained on the strainer was stripped of the major part of the absorbed liquor by compressing it in a Carver press at 5 p.s.i. pressure. The liquor obtained at this step was combined with the strained liquor and the combined liquors centrifuged to strip them of suspended matter. The solid residue from the centrifuge was combined with the residue from the Carver press. The yield was as follows:

| Liquid Extract | 2,500 grams |
|---|---|
| Fat | 840 grams |
| Fibrous protein matter some fat and moisture | 1,550 grams |
| Operation loss | 160 grams |

The liquid extract contains 25% non-volatile dry matter which includes about 2% fat (emulsified and insoluble protein). The remaining 23% represents 575 grams dry weight, or 11.5% based on the weight of the dry trachea. The liquid extract was cloudy, had a light tan color which gelled upon refrigeration to about 12° C. Except for its higher solids content and somewhat higher viscosity, the liquid extract was very similar to the extract of Example I. When freeze dried, the product was essentially identical to that obtained in Example I. In this Example the bound water, locked in the cartilage tissue was utilized in the extraction. The high solids content of the liquor obtained makes this process the most economical as less water has to be removed in the drying step.

EXAMPLE XV

Extraction of bovine trachea. Ratio of water to trachea 100/1

5 kilos of deionized water was admixed with 50 grams of well trimmed beef trachea subdivided into pieces of 1 inch in the largest dminesion. The pressure vessel and procedure were the same as in Example I. The yield of liquid extract was 4,950 grams. The extract was hazy, slightly opalescent, had a mild taste and did not gel, even after refrigeration at 3° C. When freeze dried, the product was very similar in physical characteristics to that obtained in Examples I and I-A.

EXAMPLE XVI

Extraction of bovine trachea suitable for injectable preparations

The following ingredients were used in an Enzyme pretreatment operation to remove adhering tissues prior to extraction of the cartilage tissues.

| Bovine trachea, well trimmed | 3,000 grams |
|---|---|
| Water, deionized | 6,790 |
| Acetic acid | 180 |
| Pepsin | 30 |

The trachea and the water were loaded into a jacketed stainless steel vessel equipped with a variable speed stainless steel turbine mixer. The acetic acid and pepsin were added with the mixer operating at 60 RPM. Hot water was introduced into the jacket, the temperature of the mix in the vessel raised to 55° C. and held at that temperature until the cartilage rings of the trachea were free from adhering tissues (about 5 hours). The liquid, containing the hydrolyzed tissues and most of the fat, was then drained off. The residual trachea and cartilage rings, were washed twice with deionized water (80° C.) and twice with cold deionized water until the pH of the last wash above pH 5.0. The yield was

| Trachea-cartilage rings | 1,500 grams |
|---|---|
| Deionized water | 1,500 grams |

The trachea cartilage rings and deionized water were loaded into a stainless steel pressure vessel equipped with a variable speed stainless steel turbine mixer, a steam inlet valve, theremometer, pressure gauge and pressure relief valve. The vessel was sealed, the lid clamped shut and the relief valve left open. Steam was introduced into the jacket and the mixer activated at 60 RPM. When the water in the vessel begain to boil, the steam generated was allowed to purge the air from the vessel; the relief valve was then closed. While the mixing continued, the internal pressure in the vessel was allowed to rise to 20 p.s.i.g. and maintained at about this pressure for 2½ hours. The steam in the jacket was then replaced with cooling water and the temperature in the vessel brought down to ambient temperature (about 17° C.). The material in the vessel was blanketed with nitrogen and 30 grams of a diatomaceous earth (acid washed Hyflo Supercel) filter aid was introduced into the vessel and the mixing continued for another 15 minutes. The batch was then filtered through a ceramic filter pre-coated with the same diatomaceous filter aid.

The filtrate was concentrated to 25% of its volume under vacuum with maximum pot temperature of 75° C. The concentrated filtrate was introduced, under vigorous agitation, into ten times its volume of isopropanol. The precipitated and partially dehydrated cartilage substance was filtered, washed with isopropanol and then with acetone and finally stripped of the solvents in a forced air dryer at 50°–45° C. until the loss on drying was less than 2% of the dry weight of the substance.

The procedure yielded a product that was 5.5% by weight of the crude trachea or 12.4% by weight of the cartilage rings after the enzyme treatment. The material was light gray-tan in color and was readily soluble in water of ambient temperature, forming a light tan colored solution which had a slight haze. (When the solution was filtered through a Milipore filter a sparkling clear solution suitable for use in formulating injectable preparations for clinical administration to animals or humans.

EXAMPLE XVII

The extraction was carried out as in Example III, but the concentrated filtrate in this case was dehydrated azeotropically using heptane as the azeotrope. The dehydrated material was stripped of the solvent in a forced air dryer at 45° C. until the weight loss on drying was less than 2%. The dried material was a granular friable solid which had no perceptible solvent odor and which was soluble in water at ambient temperature forming a slightly hazy light amber colored solution. The solution could be clarified via filtration.

EXAMPLE XVIII

The extraction process as in Example XV, but the concentrated filtrate in this case was dehydrated by freeze drying in a VirTis 25-SRC sublimator at a shelf temperature of +30° C. and a vacuum of 45 microns. The dried material was a flaky and very fluffy product of light amber color, soluble in water at ambient temperature forming a slightly hazy solution which could be readily clarified by filtration or by centrifuging.

What is claimed is:

1. The method of producing a biologically active cartilage product which consists of:
    admixing pieces of raw cartilage derived from a cartilage bearing animal, fish or reptile, with water in the ratio from about 1:100 to 100:1, cartilage to water,
    heating said admixture in a confined space to a predetermined pressure between 10 and about 60 pounds per square inch at a temperature in the range between about 50° C. and 150° C.,
    maintaining said admixture at said pressure and temperature for a period of time between about five minutes and five hours to form an aqueous cartilage extract containing suspended solid material, and
    separating said suspended solid material from said aqueous cartilage extract to yield a separated solid material and a separated aqueous cartilage extract.

2. The method of claim 1 which comprises concentrating said separated aqueous cartilage extract under a vacuum, said concentrated aqueous cartilage extract having a solids content of between about 45% and 65%.

3. The method of claim 1 wherein said pressure is between about 10 and about 30 pounds per square inch.

4. The method of claim 1 wherein said time period is between about 1 and 5 hours.

5. The method of claim 4 which comprises drying the separated aqueous cartilage extract.

6. The method of claim 5 wherein said drying step comprises contacting said separated aqueous cartilage extract with a liquid and precipitating the cartilage extract as a wet solid.

7. The method of claim 6 wherein said drying step comprises removing moisture from said separated aqueous cartilage extract by subjecting said extract to a temperature below 0° C. in the presence of a vacuum.

8. The method of claim 5 which comprises concentrating said separated aqueous cartilage extract under a vacuum of between about 10 and 100 torr.

9. The method of claim 5 which comprises drying said separated aqueous cartilage extract by azeotropic distillation with a hydrocarbon azeotrope.

10. The method of claim 2 wherein said raw cartilage includes a small percentage of the original fat and adhering proteinaceous tissue.

11. The method of claim 5 wherein said raw cartilage is derived from a cartilage bearing animal.

12. The method of claim 11 wherein said animal is of the bovine genus.

13. The method of claim 5 wherein said raw cartilage is derived from a fish.

14. The method of claim 13 wherein said fish is a shark.

15. The method of claim 13 wherein said separated aqueous cartilage extract is a gel at room temperature.

16. A biologically active cartilage product prepared by the process of claim 1 separating substantially all of the organs, skin and integument from cartilage derived from a cartilage bearing animal reptile or fish,
    admixing said cartilage with water in the ratio between 1:100 and 100:1 cartilage to water,
    extracting said mixture of cartilage and water at a temperature between about 105° and 125° C. and at a pressure of between about 10 and 60 pounds per square inch for a predetermined time between about 5 minutes and 5 hours, to form an aqueous cartilage extract containing suspended solid material,
    and further comprises concentrating the solid free aqueous extract under a vacuum, and
    drying said concentrated extract to a dry product.

17. The product of claim 16 wherein the concentrating step is conducted by agitating said extract in a thin film evaporator device.

18. The method of producing a biologically active cartilage product which comprises:
    admixing raw cartilage which has not been subjected to acid pepsin digestion with water, said admixture being in the ratio from 1:100 to 100:1 cartilate to water,
    heating said admixture to a temperature of between about 50° C. and 125° C. under a pressure of between about 10 and about 30 pounds per square inch,
    maintaining said admixture at said temperature and pressure for between about 5 minutes and 5 hours to form an aqueous extract containing suspended solid materials, and
    separating said suspended solid materials from said extract.

19. A shaped lipstick comprising the dried extract of claim 18 and at least one lipstick base selected from the group consisting of hydrogenated vegetable oils, lanolin waxes, lanolin alcohols, beeswax and petrolatum.

20. A shaped rectal suppository comprising from about 2% to about 5% of the biologically active cartilage product of claim 18, and a hydrogenated vegetable oil base.

21. The method of claim 18 which comprises separating said suspended solid materials from said extract by filtering said extract through a filter press.

22. The method of claim 18 which comprises separating said suspended solid materials from said extract by centrifuging said extract.

23. The method of claim 18 which comprises concentrating said extract by dehydration to form a dry material, and grinding said dry material to a fine powder.

24. A pharmaceutical formulation comprising a pharmaceutically acceptable liquid and the biologically active cartilage product of claim 20.

25. The method of claim 2 which comprises combining said separated aqueous cartilage extract with an excess of isopropanol to precipitate a solid material.

26. The method of claim 1 which comprises subdividing said raw cartilage prior to said admixing.

27. The method of claim 1 which comprises conducting said heating step in the presence of an oxidizing atmosphere.

* * * * *